(12) United States Patent
Stanfield et al.

(10) Patent No.: US 10,456,167 B2
(45) Date of Patent: Oct. 29, 2019

(54) CORING DILATOR FOR DEFINING AN APERTURE IN A TISSUE WALL

(71) Applicant: VADOVATIONS, INC., Oklahoma City, OK (US)

(72) Inventors: J. Ryan Stanfield, Edmond, OK (US); James W. Long, Oklahoma City, OK (US)

(73) Assignee: VADOVATIONS, INC., Oklahoma City, OK (US)

( * ) Notice: Subject to any disclaimer, the term of this patent is extended or adjusted under 35 U.S.C. 154(b) by 284 days.

(21) Appl. No.: 15/421,351

(22) Filed: Jan. 31, 2017

(65) Prior Publication Data

US 2017/0202575 A1 Jul. 20, 2017

Related U.S. Application Data

(63) Continuation of application No. PCT/US2014/049457, filed on Aug. 1, 2014.

(51) Int. Cl.
*A61B 17/34* (2006.01)
*A61M 1/12* (2006.01)
(Continued)

(52) U.S. Cl.
CPC ...... *A61B 17/3423* (2013.01); *A61B 17/3468* (2013.01); *A61B 17/3478* (2013.01);
(Continued)

(58) Field of Classification Search
CPC ............ A61B 17/3421; A61B 17/3423; A61B 17/3468; A61B 2017/00247;
(Continued)

(56) References Cited

U.S. PATENT DOCUMENTS 4,364,391 A * 12/1982 Toye ................. A61M 16/0472
128/207.29
5,591,191 A 1/1997 Kieturakis
(Continued)

FOREIGN PATENT DOCUMENTS

CN 102160804 A 8/2011
DE 29611170 U1 9/1996
(Continued)

OTHER PUBLICATIONS

The State Intellectual Property Office of the People's Republic of China (SIPO), The First Office Action dated Sep. 13, 2018, related Chinese patent application No. 201480081353.7, pp. 1-10, English-language translation, pp. 11-22, claims examined, pp. 23-17.
(Continued)

*Primary Examiner* — Ryan J. Severson
(74) *Attorney, Agent, or Firm* — O'Banion & Ritchey LLP; John P. O'Banion

(57) ABSTRACT

A coring tool and a dilator for defining an aperture in a tissue is presented. The system is preferably configured for generating an aperture within a ventricular wall for a method of implantation of ventricular assist devices (VAD's). The insertion tool/system includes a conduit device including a detachable dilator-coring tool and cuff which secures within a defined aperture in the tissue.

23 Claims, 10 Drawing Sheets

(51) Int. Cl.
*A61M 29/00* (2006.01)
*A61B 17/00* (2006.01)

(52) U.S. Cl.
CPC ... *A61M 29/00* (2013.01); *A61B 2017/00252* (2013.01); *A61B 2017/349* (2013.01); *A61B 2017/3425* (2013.01); *A61B 2017/3458* (2013.01); *A61M 1/122* (2014.02)

(58) Field of Classification Search
CPC .. A61B 2017/00252; A61B 2017/3425; A61B 2017/3445; A61B 2017/3454; A61B 2017/3458; A61B 2017/347; A61B 2017/349; A61M 1/122; A61M 29/00
See application file for complete search history.

(56) References Cited

U.S. PATENT DOCUMENTS

| | | | |
|---|---|---|---|
| 5,713,870 A * | 2/1998 | Yoon | A61B 17/3417 604/164.01 |
| 5,735,867 A | 4/1998 | Golser | |
| 5,755,697 A | 5/1998 | Jones et al. | |
| 5,944,732 A * | 8/1999 | Raulerson | A61B 17/3415 604/264 |
| 6,210,397 B1 | 4/2001 | Aboul-Hosn et al. | |
| 6,517,519 B1 | 2/2003 | Rosen | |
| 6,638,237 B1 * | 10/2003 | Guiles | A61F 2/2493 604/8 |
| 6,651,670 B2 * | 11/2003 | Rapacki | A61B 17/3468 128/898 |
| 6,964,652 B2 * | 11/2005 | Guiles | A61F 2/2493 604/117 |
| 7,214,234 B2 * | 5/2007 | Rapacki | A61B 17/3468 606/167 |
| 7,510,561 B2 * | 3/2009 | Beane | A61B 17/0218 606/153 |
| 7,799,041 B2 * | 9/2010 | Beane | A61B 17/0218 606/153 |
| 7,938,842 B1 | 5/2011 | Chin | |
| 8,151,791 B2 * | 4/2012 | Arlow | A61M 16/0472 128/200.26 |
| 8,226,670 B2 * | 7/2012 | Beane | A61B 17/0218 606/153 |
| 8,679,138 B2 * | 3/2014 | Beane | A61B 17/0218 606/153 |
| 8,747,394 B2 * | 6/2014 | Belson | A61B 17/00234 606/1 |
| 8,827,988 B2 * | 9/2014 | Belson | A61B 17/00234 600/117 |
| 8,858,538 B2 * | 10/2014 | Belson | A61B 17/00234 600/106 |
| 9,138,228 B2 * | 9/2015 | Vassiliades | A61B 17/11 |
| 9,161,747 B2 * | 10/2015 | Whittaker | A61B 17/3421 |
| 9,211,368 B2 * | 12/2015 | Wampler | A61M 1/101 |
| 9,737,651 B2 * | 8/2017 | Wampler | A61M 1/101 |
| 2002/0161424 A1 * | 10/2002 | Rapacki | A61B 17/3468 623/1.1 |
| 2002/0177865 A1 * | 11/2002 | McIntosh | A61B 17/32053 606/184 |
| 2004/0077987 A1 * | 4/2004 | Rapacki | A61B 17/3468 604/8 |
| 2004/0106931 A1 | 6/2004 | Guiles et al. | |
| 2005/0043781 A1 * | 2/2005 | Foley | A61F 2/2493 623/1.15 |
| 2005/0209607 A1 | 9/2005 | Lipchitz | |
| 2005/0288685 A1 * | 12/2005 | Gulles | A61F 2/2493 606/108 |
| 2006/0036313 A1 * | 2/2006 | Vassiliades | A61F 2/064 623/1.23 |
| 2006/0089707 A1 | 4/2006 | Vassiliades et al. | |
| 2007/0265643 A1 * | 11/2007 | Beane | A61B 17/11 606/153 |
| 2008/0076959 A1 * | 3/2008 | Farnan | A61M 1/12 600/16 |
| 2012/0089181 A1 * | 4/2012 | Shanley | A61B 17/0057 606/223 |
| 2013/0245361 A1 * | 9/2013 | Wampler | A61M 1/101 600/16 |
| 2016/0144087 A1 * | 5/2016 | Wampler | A61M 1/101 600/16 |
| 2017/0202575 A1 * | 7/2017 | Stanfield | A61M 29/00 |

FOREIGN PATENT DOCUMENTS

| | | |
|---|---|---|
| EP | 2233165 A2 | 9/2010 |
| EP | 2233165 A3 | 9/2010 |
| EP | 3181074 A1 | 6/2017 |
| JP | H0819600 A | 1/1996 |
| WO | 0112086 A1 | 2/2001 |
| WO | 03001980 A2 | 1/2003 |

OTHER PUBLICATIONS

European Patent Office (EPO), Communication (extended European search report) dated Apr. 18, 2018, related European patent application No. 14898646.8, pp. 1-7, claims searched, pp. 8-10.
Japan Patent Office (JPO), first office action dated May 22, 2018, related Japanese patent application No. 2017-526035, pp. 1-6, partial translation, pp. 7-12, claims examined, pp. 13-16.
Korean Intellectual Property Office (KIPO), International Search Report and Written Opinion dated Apr. 21, 2015, related PCT International Application No. PCT/US2014/049457, pp. 1-13, with claims searched, pp. 14-18.
IP Australia, Examination report No. 1 for standard patent application dated May 13, 2019, related Australia patent applicadtion No. 2014402333, pp. 1-3, claims examined, pp. 4-7.

* cited by examiner

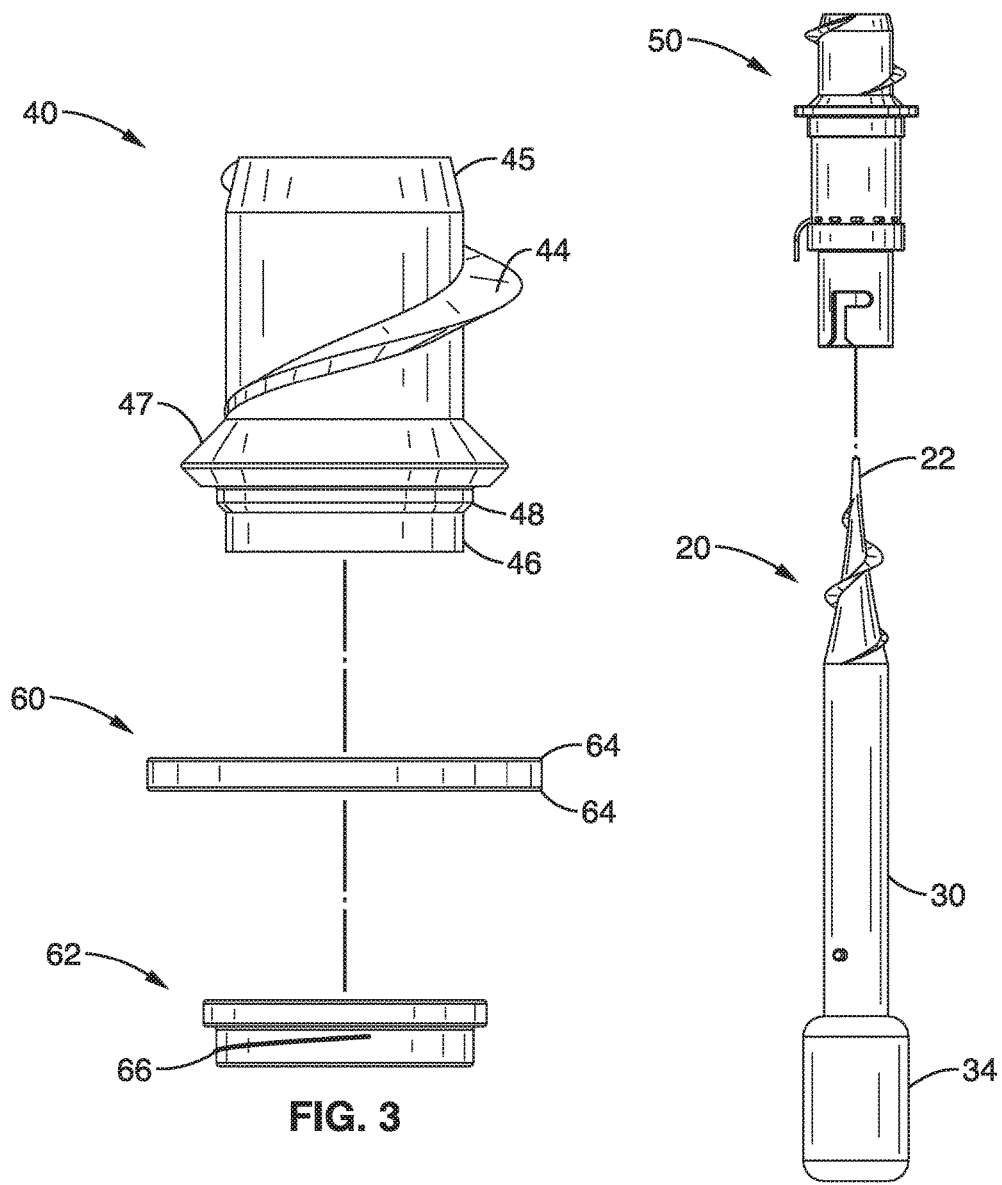

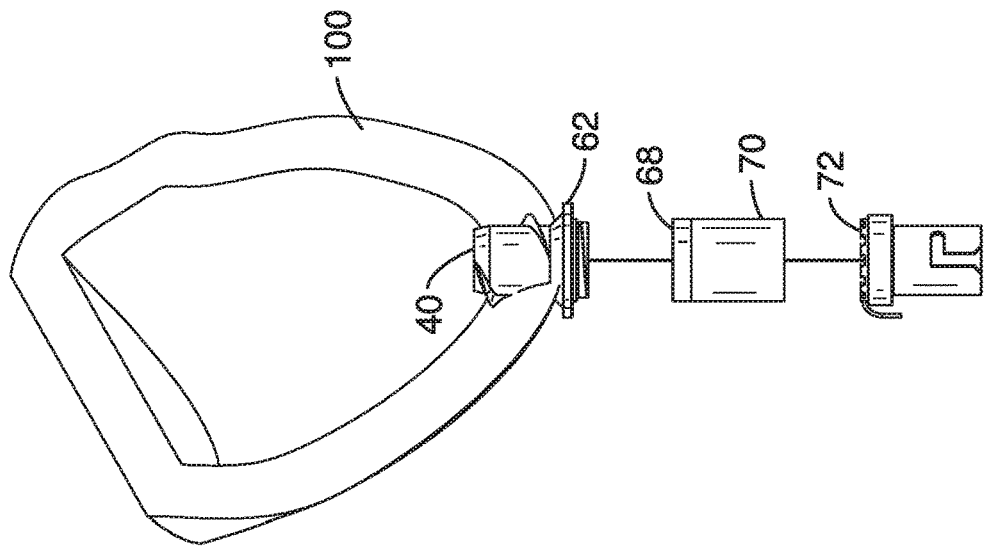
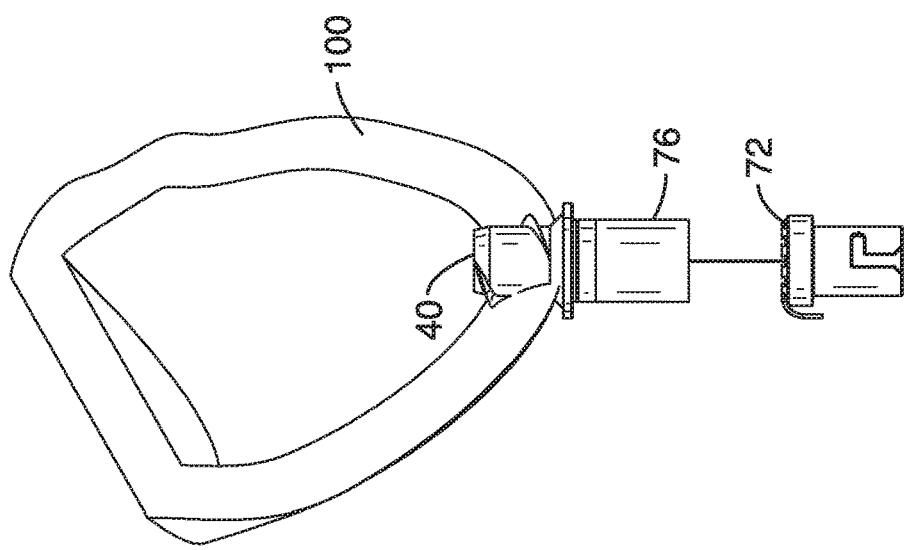
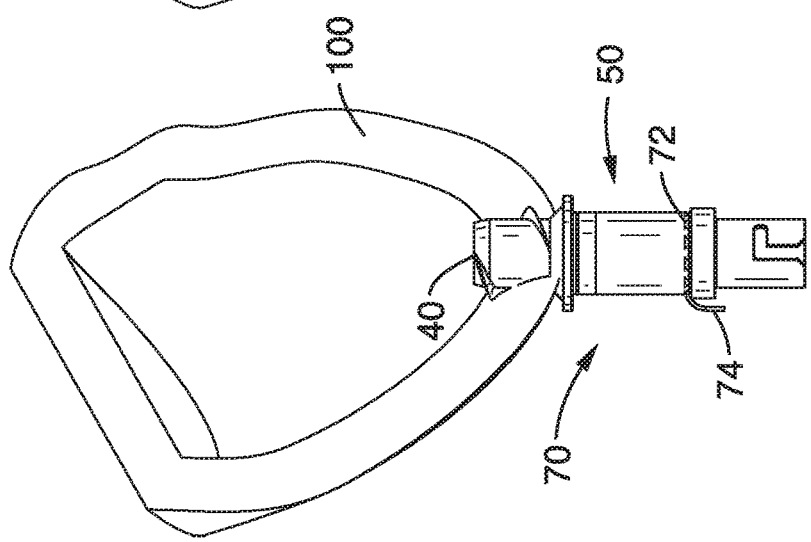

CORING DILATOR FOR DEFINING AN APERTURE IN A TISSUE WALL

CROSS-REFERENCE TO RELATED APPLICATIONS

This application is a 35 U.S.C. § 111(a) continuation of PCT international application number PCT/US2014/049457 filed on Aug. 1, 2014, incorporated herein by reference in its entirety.

The above-referenced PCT international application was published as PCT International Publication No. WO 2016/018434 on Feb. 4, 2016, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE DISCLOSURE

1. Field of the Disclosure

This disclosure pertains generally to systems and methods for generating apertures in body tissues, and more particularly to systems and methods for generating apertures in vasculature.

2. Description of Related Art

Ventricular assist devices (VAD's) are mechanical circulatory devices that are used to partially or completely replace the function of a failing heart. Several continuous-flow ventricular assist devices (VADs) have been developed over the last decade. Compared with pulsatile-output predecessors, continuous-flow VADs are smaller, quieter, and easier to implant. Despite these advances, many patients still suffer significant morbidity or even death in association with the implantation procedure itself.

In conventional VAD implantation with cardiopulmonary bypass (CPB), normothermia is maintained and the heart continues to beat while a cylindrical blade excises a core of myocardium from the apex. A VAD sewing ring is then sutured to the margins of the apical hole.

Another technique is off-Pump VAD Implantation without CPB, such as that used for placement of a HeartMate® II LVAD (Thoratec Corporation; Pleasanton, Calif.). Typically, deep pericardial sutures or lap pads are used to facilitate this. In some instances, hemodynamic stability cannot be maintained, and CPB must be initiated.

Many existing procedures generally require one or more cardiac surgeons and rapid and risky exchanges between the surgeon's finger and knife or other instrument.

Accordingly, an object of the present disclosure is to provide tools and techniques to eliminate some of these steps and facilitate the creation of a clean circular hole without retained myocardial fragments.

BRIEF SUMMARY OF THE DISCLOSURE

An aspect of the present disclosure is a coring tool and a dilator for defining an aperture in a tissue. In particular, the system is preferably configured for generating an aperture within a ventricular wall for a method of implantation of ventricular assist devices (VAD's). The insertion tool/system includes a conduit device including a detachable dilator-coring tool and cuff which secures within a defined aperture in the tissue.

Further aspects of the disclosure will be brought out in the following portions of the specification, wherein the detailed description is for the purpose of fully disclosing preferred embodiments of the disclosure without placing limitations thereon.

BRIEF DESCRIPTION OF THE SEVERAL VIEWS OF THE DRAWING(S)

The disclosure will be more fully understood by reference to the following drawings which are for illustrative purposes only:

FIG. 3 is a close-up view of the cuff, sewing ring and lock ring of the coring and a dilator system of FIG. 2.

FIG. 4 is a side view of the coring assembly separated from the dilator assembly of FIG. 1.

FIG. 8A and FIG. 8B show side views of the coring assembly in initial (FIG. 8A) and partially removed (FIG. 8B) states.

FIG. 8C is a side view of an alternative coring assembly with a lower portion being unthreaded from an upper portion.

DETAILED DESCRIPTION OF THE DISCLOSURE

FIG. 1 through FIG. 4 show a system 10 that acts both as a coring tool and a dilator for defining an aperture in a tissue wall in accordance with the present disclosure. In particular, system 10 is preferably configured for generating an aperture within a ventricular wall for a method of implantation of ventricular assist devices (VAD's). The insertion tool/system 10 provides a conduit device including a detachable dilator-coring tool and cuff which secures within a defined aperture in the tissue.

Figure 1:
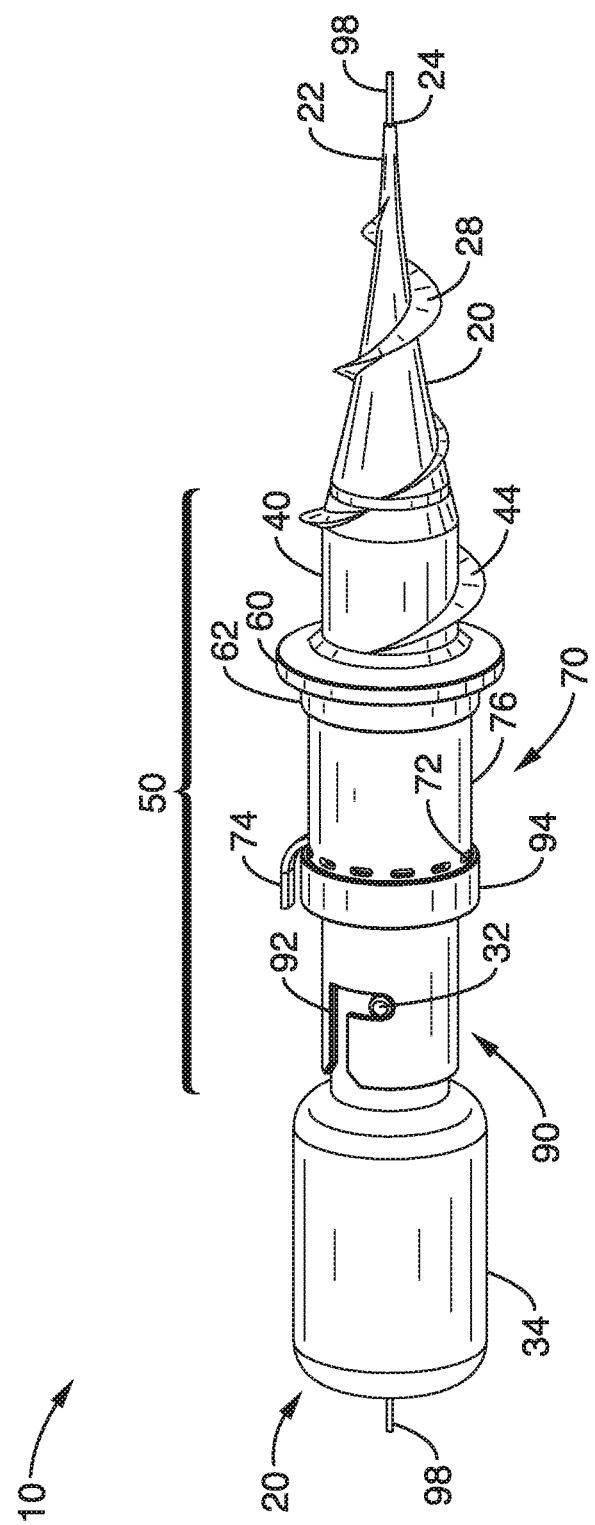
FIG. 1 is a perspective view of coring and a dilator system for defining an aperture in a tissue wall in accordance with the present disclosure.
Figure 2:
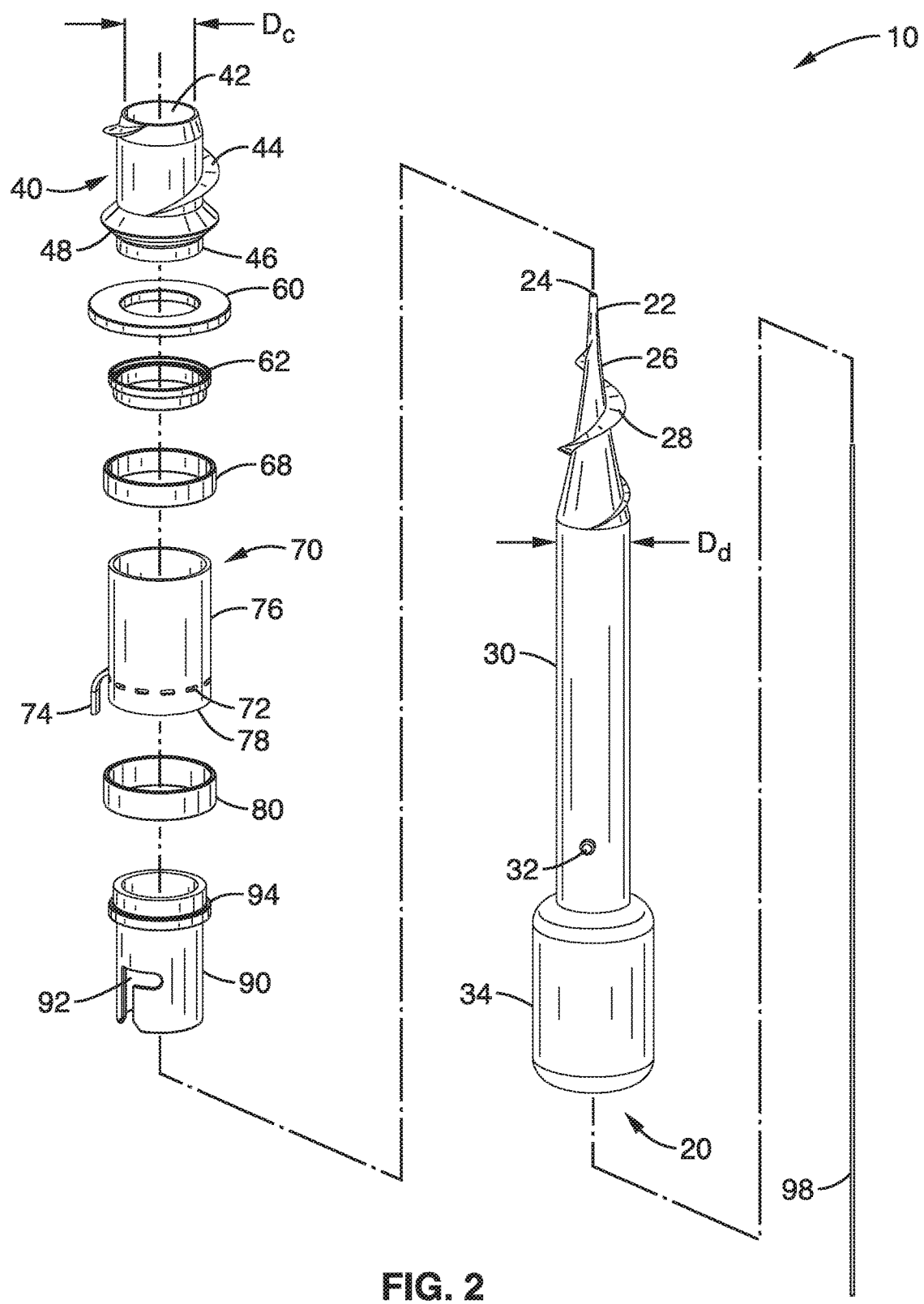
FIG. 2 is an exploded view of the coring and a dilator system of FIG. 1.
Figure 5D:
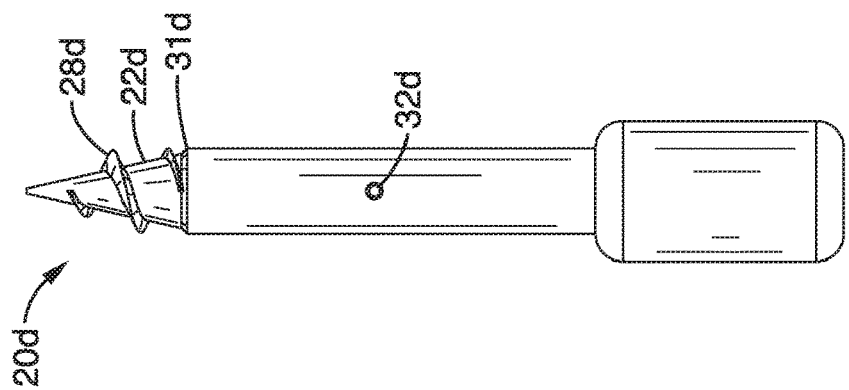
FIG. 5A through FIG. 5D show various alternative embodiments of the dilator assembly of FIG. 1.
Figure 5C:
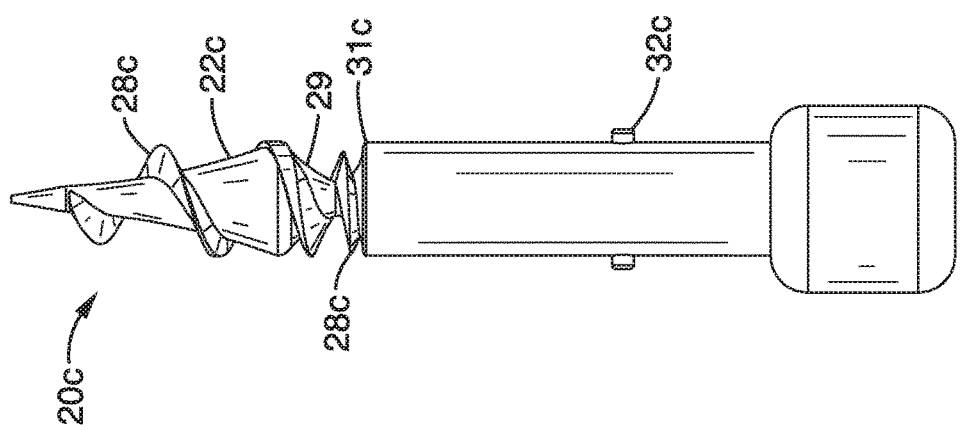
Figure 5B:
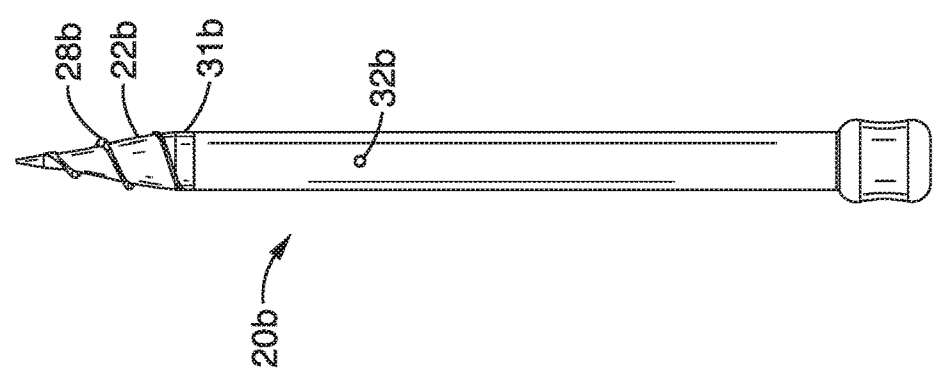
Figure 5A:
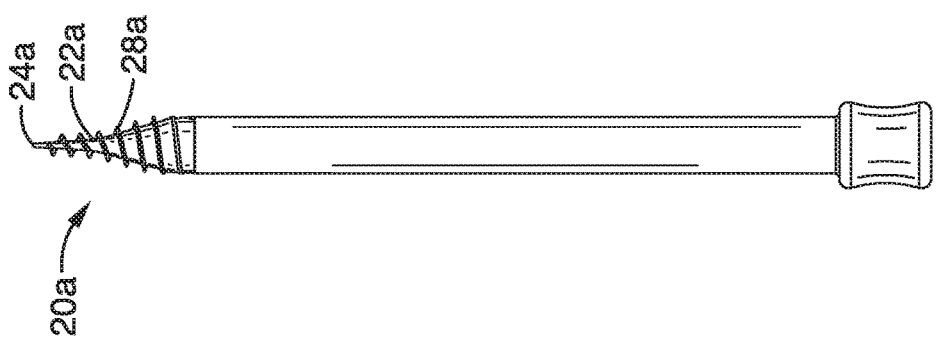

FIG. 1 shows a perspective view of coring and a dilator system 10 for defining an aperture in a tissue wall, and FIG. 2 is an exploded view of the coring and a dilator system 10. In FIG. 1, the dilator 20 is shown installed over guide wire 98 (e.g. with central aperture 24), with coring assembly 50 disposed and locked in position over dilator 20.

While the systems and methods of the present technology preferably do not employ removal/resection of tissue (e.g. commonly referred to as coring), it is appreciated that the term "coring" as used herein shall be broadly construed where applicable. For purposes of this description, the term "coring," as used in the coring and dilator system 10, coring assembly 50, coring handle 90, etc., shall be defined as the process of generating an aperture in tissue by stretching/expanding tissue, cutting/removing tissue, or a combination of both.

The coring assembly 50 is configured to be slidably received (preferably pre-assembled as shown in FIG. 4) over the elongate shaft 30 (see FIG. 2) of the dilator 20 such that protrusion 32 on the shaft 30 aligns with key slot 92 of the coring assembly handle 90. With the coring assembly 50 rotated in place via protrusion 32 and key slot 92 as shown in FIG. 1, the threads 44 of the coring assembly 50 cuff 40 are aligned with corresponding threads of 28 of conical section 26 of the dilator 20. Conical section 20 terminates at distal tip 22 and the distal aperture of central channel 24.

As shown in FIG. 1 and FIG. 2, the dilator 20 comprises a proximal handle 34 that allows for manual insertion of the system 10 into a target region of tissue and rotation of the dilator/coring assembly to core into and dilate the tissue.

As best shown in FIG. 2, the coring assembly 50 includes a plurality of lock rings 62, 68 and 80 that facilitate assembly of the various components (e.g. cuff 40, sewing ring 60, flexible sheath 70 and handle 90) with respect to each other. FIG. 3 shows a close-up view of the cuff 40, sewing ring 60 and lock ring 62 of the coring assembly 50. The cuff has helical threads 44 that align with the threads 28 on dilator 20 upon securing the coring assembly 50 to the dilator 20. In some embodiments, the leading edge of the cuff 45 (see FIG. 3) maybe chamfered such that it tapers down to and aligns with the conical shaped section 26 of dilator 20. This helps the cuff 40 to cut through the tissue without damaging it.

In addition to the chamfer on the leading edge 45, in some embodiments, the cuff 40 may also have a chamfer 47 beneath the threads 44 to prevent the cuff 40 from entering completely into the organ or tissue wall (i.e. act as a stop to insertion). In other embodiments, a flexible flange or a sewing ring 60 maybe compression fitted onto beveled surface 48 of cuff 40 to allow the cuff 40 to be secured (i.e. sewn in to) the tissue or organ wall. Chamfers 64 may be generated along with the sewing ring 60 to act to direct the tissue inwards and eliminate leak paths.

As seen in FIG. 1 and FIG. 2, the outer diameter $D_d$ of cylindrical section 30 on dilator and inner diameter $D_c$ of central aperture 42 of cuff 40 may be closely matched such that the radial clearance between the two is minimized.

For assembly, the sewing ring may be press-fit on surface 48 of the cuff 40, and lock ring press fit on surface 46 of the cuff to hold the sewing ring in place. Lock ring 62 may also comprise thread 66 for coupling to the flexible sheath 70.

Alternatively, a second lock ring 68 (see FIG. 2) may be used to secure the sheath 70 to the first lock ring 62.

As seen in FIG. 1 and FIG. 2, the bottom portion 78 of the sheath 70 may be secured to flange 94 of the coring assembly handle 90 via a lower lock ring 80.

The flexible sheath may be fit with a circumscribing perforation 72 and pull cord 74 for separating the lower portion of the coring assembly 50 (made up of the bottom sheath portion 78, lower lock ring 80, and handle 90) from the upper portion of the coring assembly 50 (made up of the upper sheath portion 76 cuff 40, and all intervening parts). In an alternative configuration, the sheath is un-interrupted, and screws off from the upper portion of the coring assembly 50 via the thread 66 in the lock ring 62. In both configurations, the removed lower portion of the coring assembly allows for access to the dilated anatomy and delivery of instruments/devices for treatment or diagnostic purposes.

The dilator 20 and coring assembly 50 provide a system 10 that acts both as a coring tool and a dilator for defining an aperture in the tissue wall. In a preferred embodiment shown in FIGS. 1, 3 and 4, the dilator 20 has a concave-conical shape tip 26 with helical threads 28 on its outer diameter. Such shape beneficially allows for simultaneous coring and dilation of the organ wall. In preferred embodiments, the dilator 20 may be made from a flexible polymeric material allowing it to flex.

Referring now to FIG. 5A through FIG. 5D, the dilator 20 may comprise a plurality of different embodiments (e.g. 20a through 20d) that may have varying tapered/conical shapes and threads that helps in coring and dilating the tissue or organ wall.

The embodiment of dilator 20a comprises a sharp leading edge 24a to the conical head 22a which helps in initial incision and insertion in tissue or organ wall. The threads 28a may also have a smaller profile to ease insertion.

In the embodiment of dilator 20b, the proximal end of the conical section 22b and threads 28b are followed by a short cylindrical section 31b before the threads 44 on the cuff 40 begin to engage with the tissue wall. The radial clearance between the outer diameter of cylindrical section 31b on dilator and inner diameter of central aperture 42 of cuff 40 maybe very minimal. This cylindrical section 31b prevents the leading edge of cuff 40 from grabbing cored tissue.

The embodiment of dilator 20c comprises a conical tapered tip 22c having a recessed neck region 29 (e.g. having an hourglass shape) along with helical threads 28c. The neck region 29 enables the dilator to have continuous helical threads 28c without losing thread depth at the dilator—cuff junction 31c where dilator threads 28c end and the threads 44 in cuff 40 begin. It is appreciated that in some embodiments, the neck region may be void of threads 28c.

In the embodiment of dilator 20d, the proximal end of the conical section 22d and threads 28d are followed by a short tapering section 31d.

As shown in FIG. 5A through FIG. 5d, dilator configurations 20a to 20d may have no, single or multiple pegs 32b, 32c, 32d near or distal to the handle 34, and the cuff handle 90 cutout 92 may be positioned accordingly such that when assembled by inserting the dilator 20 into cuff assembly 50, the peg 32b, 32c, 32d in the dilator aligns with the cut-out 92 in cuff handle 90, which makes the device turn as a single unit while coring and dilating the tissue.

FIG. 6 through FIG. 10 show a method for implanting a conduit and/or a port for ventricular assist devices to treat a vascular condition using the coring/insertion assembly 10 of the present disclosure. It is appreciated that the method shown in FIG. 6 through FIG. 10 is a specific example of application of coring/dilator system 10 for implantation of a left ventricular assist device, and coring/dilator system 10 may be used for a variety of procedures (e.g. other VAD procedures such as RVAD, BIVAD or the like) in the human body where a port or opening through a region of tissue is desired.

Figure 6:
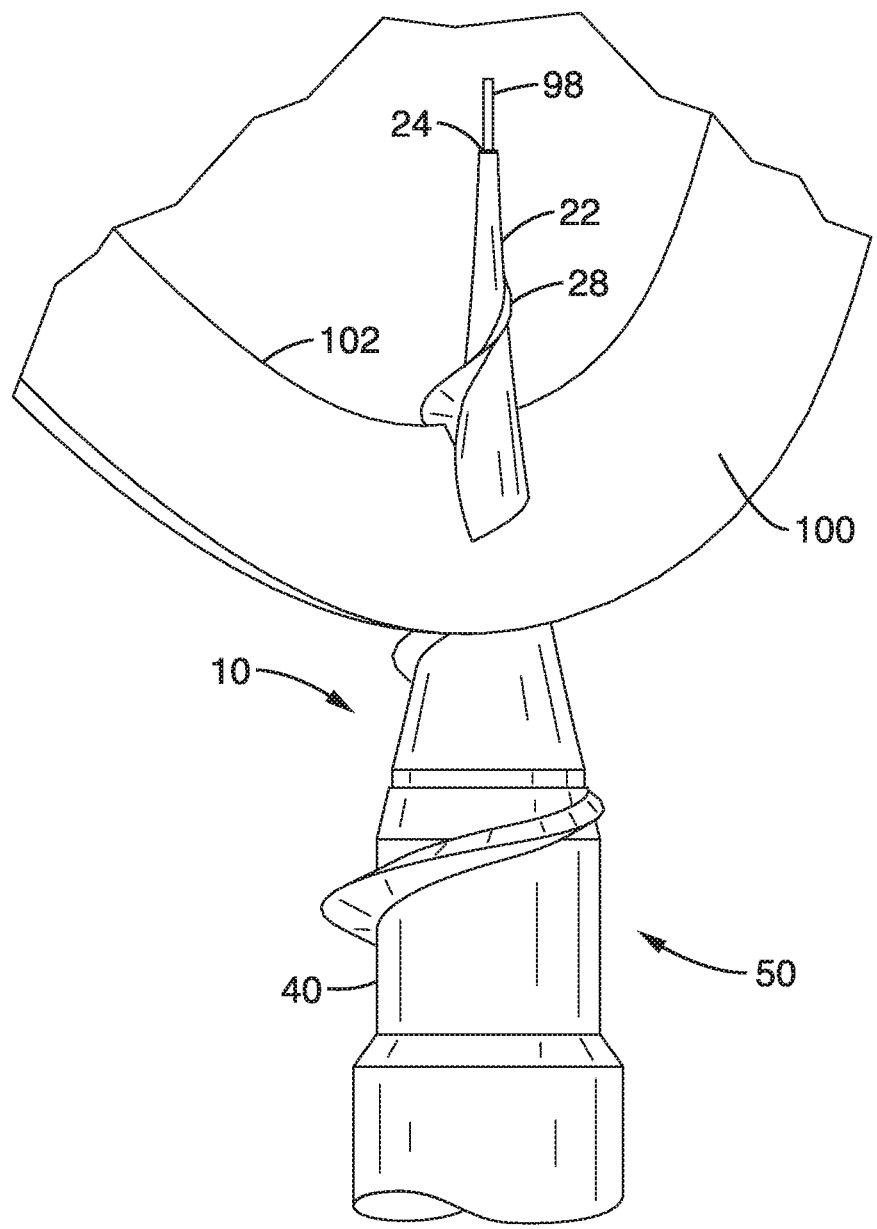
FIG. 6 is a schematic view of the coring and a dilator system of FIG. 1 being inserted into a wall of a patient's left ventricle.

As shown in FIG. 6, a guide wire 98 is passed through the heart tissue 100 and into the ventricle 102 to provide access to the tissue surface. The coring/dilator assembly 10 is then inserted over the guide wire 98 and into the defined tissue surface 100 by turning the assembly 10. Minimal force may be applied to advance the coring/dilator assembly 10, as the helical threads 28 guide the tool by coring and dilating the wall of the tissue 100. The conical tip 22 of the dilator 20 gradually dilates the tissue to open the tissue from the smaller diameter at distal opening 24 to the larger diameter of the cuff 40.

Figure 7:
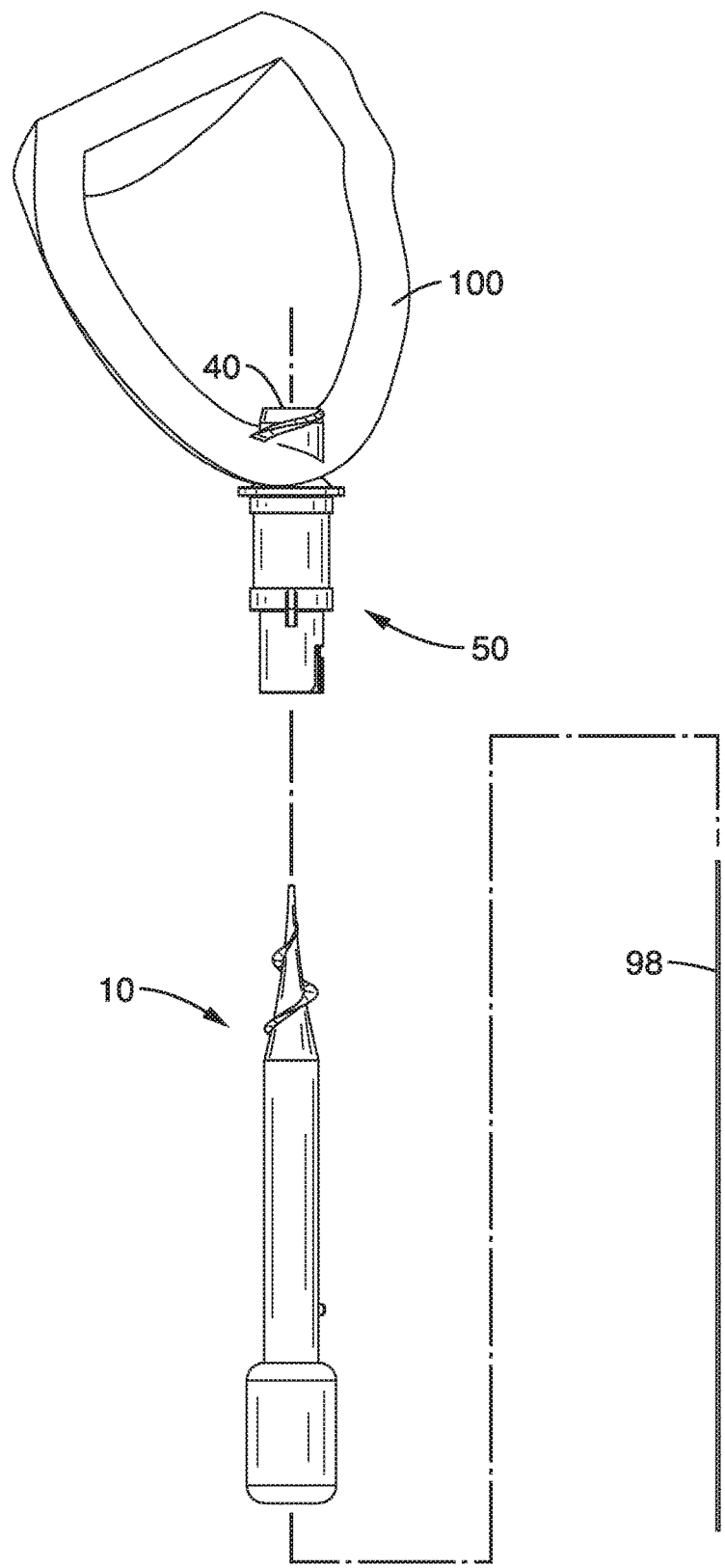
FIG. 7 is a schematic view of the dilator assembly being pulled from an embedded coring assembly at the wall of a patient's left ventricle.

Referring now to FIG. 7, the coring/dilator assembly 10 continues to advance into and dilate the tissue 100 until the cuff threads 44 engage the tissue such that the beveled surface 47 contacts the apex of tissue 100 Once the cuff 40 is anchored firmly in place, the dilator 20 is removed by rotating (such that protrusion(s) 32 advance along slot 92), and pulling it out.

According to one embodiment of the present disclosure shown in FIG. 8A and FIG. 8B, the coring assembly 50 may comprise a perforated silastic sleeve 70. The handle portion 90 of the coring assembly 50 may be detached by pulling the drawstring 74 along the perforation 72, leaving the cuff 40 and upper portion 76 of the sleeve in place while the lower portion 78 and handle portion 90 are removed.

In an alternative embodiment shown in FIG. 8C, the lock ring 62 may have threads 66 (see FIG. 3) such that the entire sleeve 70 and handle portion 90 may be screwed loose from the cuff 40. In this embodiment, the silastic sleeve 70 may be bonded to the lock ring 68 that threads on to the upper lock ring 62 or cuff 40.

In the embodiments shown in FIG. 8A through 8C, the silastic sleeve 70 is configured to be manually collapsible such that the sleeve 70 can be clamped shut to prevent blood loss from the heart during parts of the procedure.

Figure 9A:
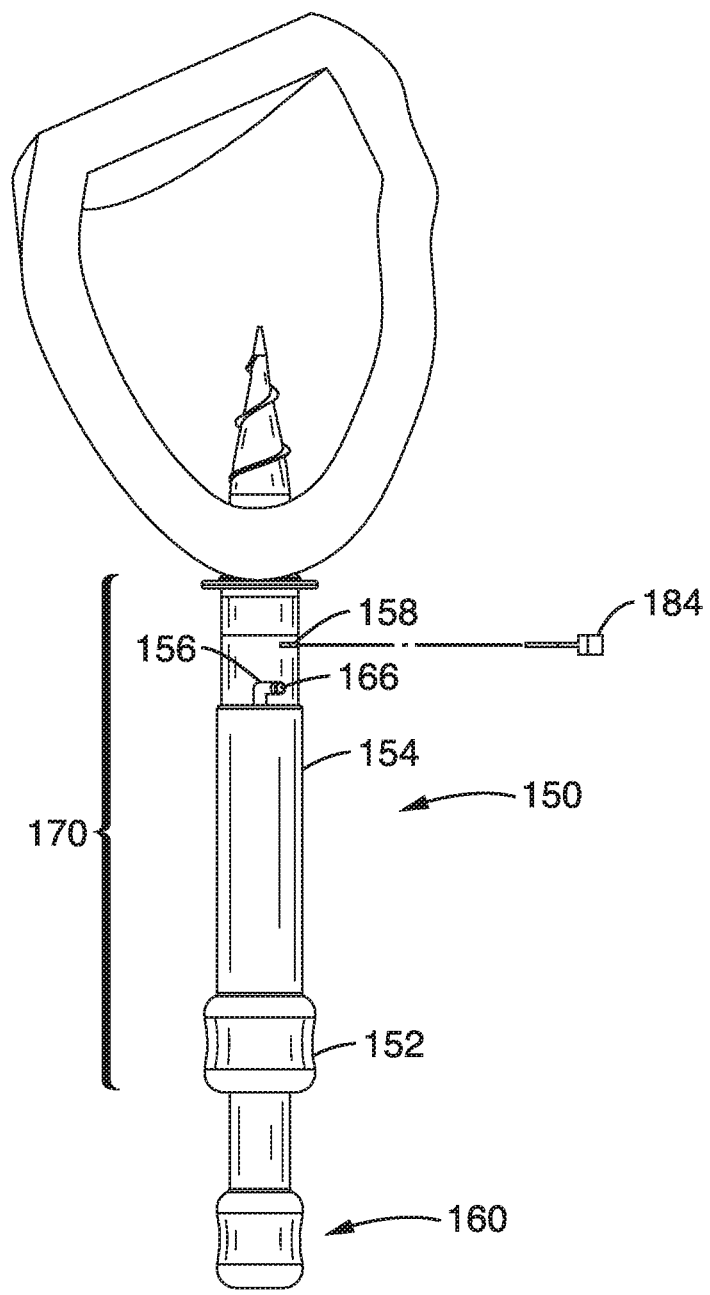
FIG. 9A and FIG. 9B show side views of an alternative embodiment of a coring and a dilator system incorporating a plug for cutting off blood flow.
Figure 9B:
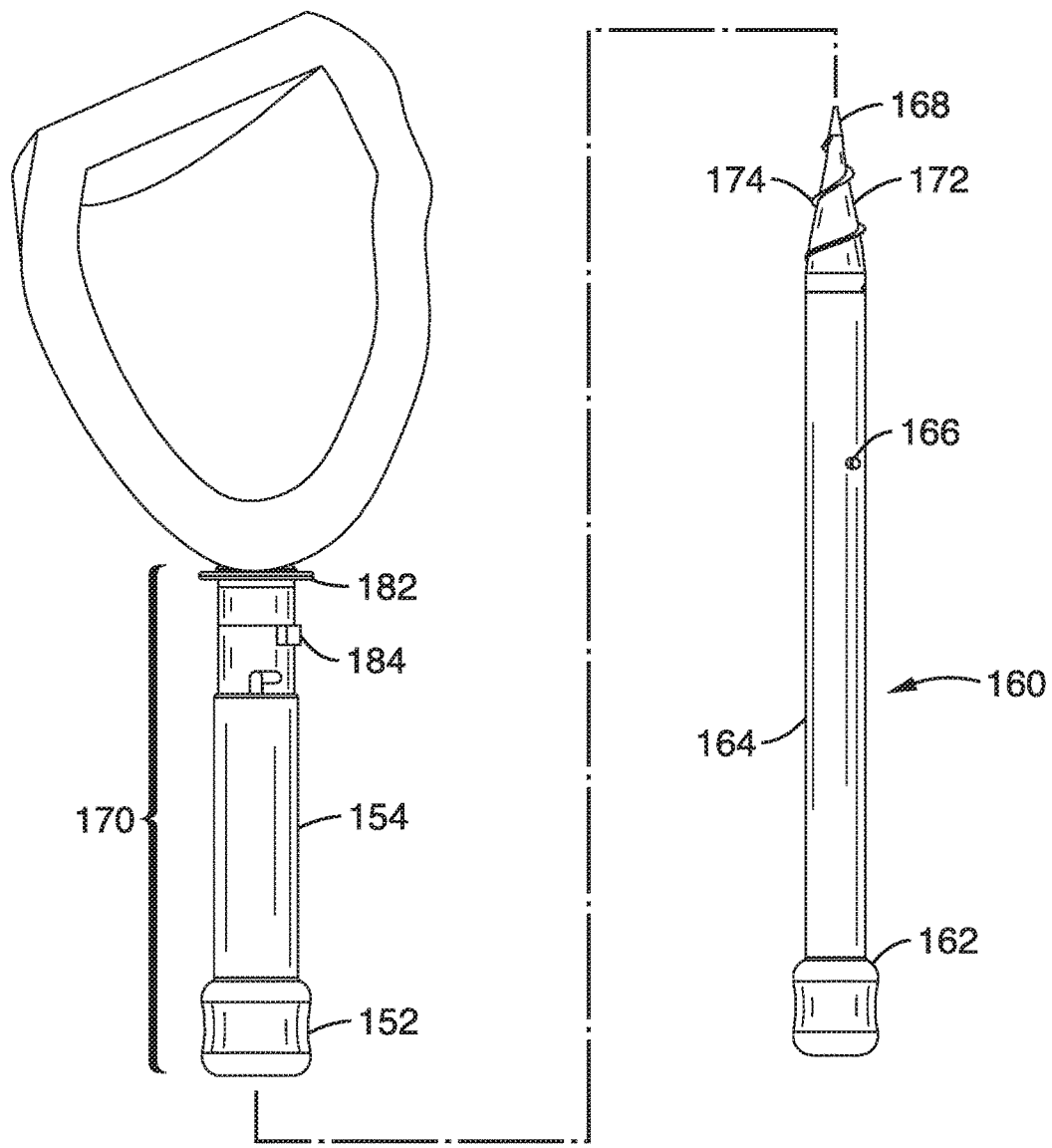

In coring/dilator system 150 shown in FIGS. 9A and 9B, the coring assembly has a rigid sheath with a plug for cutting off flow. The dilator 160 functions similar to dilator 20 in that the distal tip 168 of conical section 172 bores into the tissue 100 via threads 174 upon rotation of the system 150. The dilator 160 comprises an elongate body 164 having a handle 162 on the proximal end and protrusion 166 for keying with key slot 156 of the coring assembly 180. The coring assembly 170 comprises an elongate tubular body 154, handle 152 and a flange 182 for sewing/attachment of the cuff 40 to the tissue 100.

Elongate tubular body 154 may comprise a slit 158 for receiving a disc-shaped plug 184. As shown in FIG. 9B, the dilator 160 is removed from the coring assembly 170. Immediately after the dilator is removed, the plug 184 is inserted into the slit 158 and cuts off the flow of blood in the elongate tubular body 154, thus maintaining hemostasis.

Figure 10:
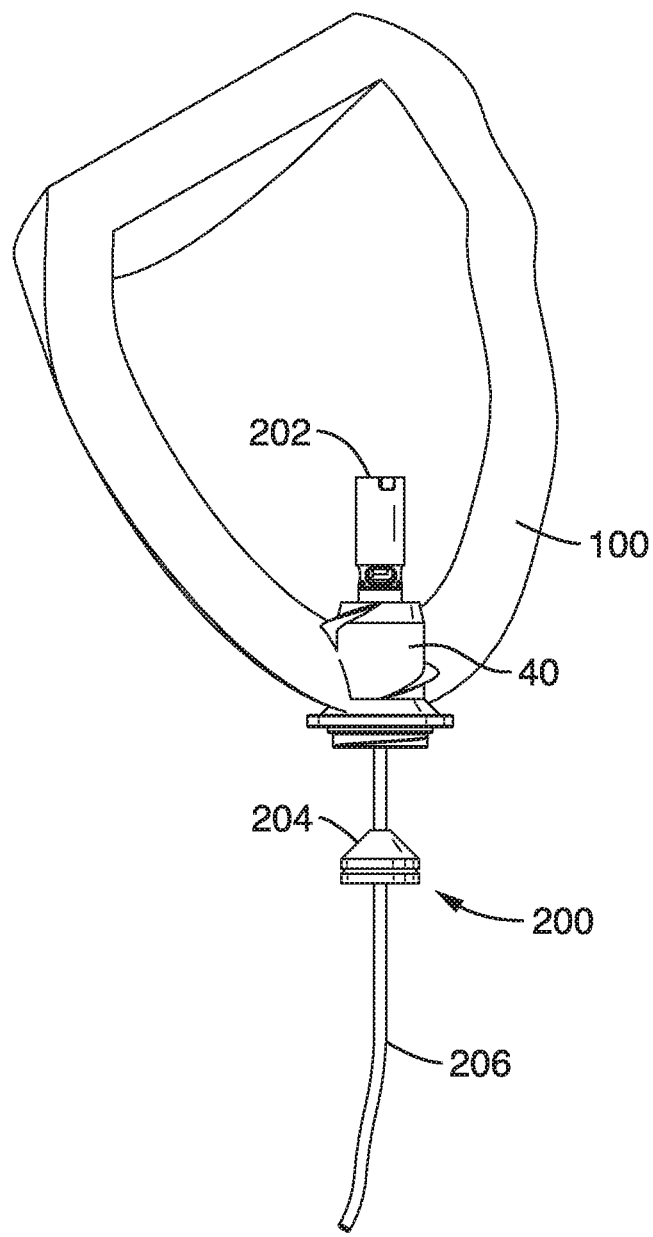
FIG. 10 shows a view of a VAD being directed into the left ventricle via a port created by the coring assembly of the present disclosure.

Referring now to FIG. 10, with the cuff 40 embedded in the tissue 100, a port is created for insertion of instruments for treatment or diagnostic of the patient. In a preferred embodiment, the instrument comprises LVAD 200 comprising a small pump 202 disposed at the distal end of conduit or catheter 206. Catheter 206 may comprise conduit for transmission of blood/fluids from one location or another, cabling for electrical operation of pump 202, or both. Pump 202 is configured to transport blood from the left ventricle to assist in cardiac function.

The conduit 206 may also comprise a hemostatic plug 204 that can be threaded into or otherwise fastened to the proximal opening of cuff 40, effectively shutting the access port and preventing leakage through the cuff 40.

In some embodiments, the plug 204 is over-molded onto the pump conduit 206, and serves as an exit site for the cable through the cuff.

According to some embodiments, the insertion tool 10, 150 may be used to dilate an initial aperture on tissue surface defined by the coring assembly 50. Because the tissue 100 is stretched rather than cut (i.e. cored) the remaining aperture in the tissue upon removal of the cuff 40 is much smaller, and can be more easily restored to a closed state.

Although some of the embodiments described herein are directed to a conduit device and a system for implanting ventricular assist devices (VAD) it should be understood that the system may also be used as, but is not limited to, a conduit or an access port for various minimally invasive delivery techniques and/or devices (e.g. cameras or other diagnostic/imaging devices, ablation/nerve conduction instruments, etc.) to provide controlled access to the heart or other body lumen and repair native blood vessels and/or tissues to treat a variety of vascular conditions.

From the discussion above it will be appreciated that the disclosure can be embodied in various ways, including but not limited to the following:

1. An apparatus for defining an aperture in a tissue wall, comprising: a dilator having a tapered distal tip for piercing tissue in said tissue wall; and a cuff having a central aperture for receiving the cuff over the dilator; wherein in an assembled configuration, the cuff is configured to seat on the dilator at a location proximal to the distal end; wherein the cuff and dilator in the assembled configuration are configured to be inserted into the tissue by introducing the distal end of the dilator into the tissue and advancing the distal end of the dilator to dilate the tissue until the cuff is seated within the tissue wall; and wherein the dilator is configured to be retracted from the cuff such that the cuff remains in the tissue wall to form a port via the central aperture of the cuff.

2. An apparatus as in any of the previous embodiments: wherein the distal end of the dilator has one or more threads at said distal end; and wherein the one or more threads are configured for engaging the tissue and advancing the dilator into the tissue upon rotation of the dilator.

3. An apparatus as in any of the previous embodiments: wherein the cuff comprises one or more threads matching the one or more threads of the dilator; and wherein the one of more cuff threads are configured to further advance the cuff into the tissue upon rotation of the dilator.

4. An apparatus as in any of the previous embodiments, wherein the dilator comprises a central through-hole for guiding the dilator over a guide-wire.

5. An apparatus as in any of the previous embodiments, the cuff further comprising a collapsible sleeve for closing the central aperture upon removal of the dilator, thereby substantially preventing fluid flow through the central aperture.

6. An apparatus as in any of the previous embodiments, the cuff further comprising a plug for closing the central aperture upon removal of the dilator, thereby substantially preventing fluid flow through the central aperture.

7. An apparatus as in any of the previous embodiments, further comprising: a coring handle; the coring handle configured to be coupled proximal to the cuff to form a coring assembly; and the coring handle having a keying slot configured to interface with a protrusion on the dilator for preventing radial and axial advancement of the cuff with respect to the dilator.

8. An apparatus as in any of the previous embodiments, wherein the coring handle is configured to be releasably attached to the cuff such that the coring handle may be detached from the cuff upon removal of the dilator.

9. An apparatus as in any of the previous embodiments, wherein the distal end of the dilator comprises a tapered conical profile configured to dilate the tissue upon advancement of the dilator within said tissue wall.

10. An apparatus as in any of the previous embodiments, said coring assembly further comprising a sewing ring for attaching the cuff to the tissue wall.

11. An apparatus as in any of the previous embodiments, the central aperture of the cuff configured to allow advancement of an instrument through said tissue wall.

12. A system for delivering a ventricular assist device (VAD) through a tissue wall of the heart, comprising: a dilator having a tapered distal tip for piercing tissue in said tissue wall; and a cuff having a central aperture for receiving the cuff over the dilator; wherein in an assembled configuration, the cuff is configured to seat on the dilator at a location proximal to the distal end; wherein the cuff and dilator in the assembled configuration are configured to be inserted into the tissue by introducing the distal end of the dilator into the tissue and advancing the distal end of the dilator to dilate the tissue until the cuff is seated within the tissue wall; and wherein the dilator is configured to be retracted from the cuff such that the cuff remains in the tissue wall to form a port into the heart via the central aperture of the cuff.

13. A system as in any of the previous embodiments: wherein the distal end of the dilator has one or more threads at said distal end; and wherein the one or more threads are configured for engaging the tissue and advancing the dilator into the tissue upon rotation of the dilator.

14. A system as in any of the previous embodiments: wherein the cuff comprises one or more threads matching the one or more threads of the dilator; and wherein the one of more cuff threads are configured to further advance the cuff into the tissue upon rotation of the dilator.

15. A system as in any of the previous embodiments, wherein the dilator comprises a central through-hole for guiding the dilator over a guide-wire.

16. A system as in any of the previous embodiments, the cuff further comprising a collapsible sleeve for closing the central aperture upon removal of the dilator, thereby substantially preventing blood flow through the central aperture.

17. A system as in any of the previous embodiments, the cuff further comprising a plug for closing the central aperture upon removal of the dilator, thereby substantially preventing fluid flow through the central aperture.

18. A system as in any of the previous embodiments, further comprising: a coring handle; the coring handle configured to be coupled proximal to the cuff to form a coring assembly; and the coring handle having a keying slot configured to interface with a protrusion on the dilator for preventing radial and axial advancement of the cuff with respect to the dilator.

19. A system as in any of the previous embodiments, wherein the coring handle is configured to be releasably attached to the cuff such that the coring handle may be detached from the cuff upon removal of the dilator.

20. A system as in any of the previous embodiments, wherein the distal end of the dilator comprises a tapered conical profile configured to dilate the tissue upon advancement of the dilator within said tissue wall.

21. A system as in any of the previous embodiments, said coring assembly further comprising a sewing ring for attaching the cuff to the tissue wall.

22. A system as in any of the previous embodiments, the system further comprising a VAD: wherein the central aperture of the cuff is configured to allow advancement of the VAD into the heart.

23. A system as in any of the previous embodiments: wherein the VAD is disposed on a distal end of a conduit; wherein a plug is disposed on the conduit proximal to the VAD; and wherein the plug is sized to form a seal to block flow of blood from the central aperture when the VAD is positioned within the heart. Although the description above contains many details, these should not be construed as limiting the scope of the disclosure but as merely providing illustrations of some of the presently preferred embodiments of this disclosure.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for defining an aperture in a tissue wall, comprising:
   a dilator having a tapered distal tip end for piercing tissue in said tissue wall;
   a cuff having a central aperture for receiving the cuff over the dilator; and
   a coring handle releasably coupled proximal to the cuff to form a coring assembly;
   wherein the coring assembly is configured to engage the dilator such that the dilator and coring assembly rotate as a single unit upon manual rotation of the dilator;
   wherein in an assembled configuration, the coring assembly is configured to seat on the dilator at a location proximal to the distal end;
   wherein the cuff and dilator in the assembled configuration are configured to be inserted into the tissue by introducing the distal end of the dilator into the tissue and advancing the distal end of the dilator to dilate the tissue until the cuff is seated within the tissue wall;
   wherein the dilator is configured to be retracted from the coring assembly such that the cuff remains in the tissue wall to form a port via the central aperture of the cuff; and wherein the coring handle is configured to be detached from the cuff upon removal of the dilator.

2. An apparatus as recited in claim 1:
wherein the distal end of the dilator has one or more threads at said distal end; and
wherein the one or more threads are configured for engaging the tissue and advancing the dilator into the tissue upon rotation of the dilator.

3. An apparatus as recited in claim 2:
wherein the cuff comprises one or more threads matching the one or more threads of the dilator; and
wherein the one of more cuff threads are configured to further advance the cuff into the tissue upon rotation of the dilator.

4. An apparatus as recited in claim 3, wherein the coring handle comprises a keying slot configured to interface with a protrusion on the dilator for preventing radial and axial advancement of the cuff with respect to the dilator upon rotation and advancement of the dilator.

5. An apparatus as recited in claim 4, wherein the keying slot of the coring handle and protrusion on the dilator are located such that the one or more threads of the dilator are aligned with the one or more threads of the cuff.

6. An apparatus as recited in claim 4, said coring assembly further comprising a sewing ring for attaching the cuff to the tissue wall.

7. An apparatus as recited in claim 1, wherein the dilator comprises a central through-hole for guiding the dilator over a guide-wire.

8. An apparatus as recited in claim 1, the coring assembly further comprising a collapsible sleeve proximally coupled to the cuff for closing the central aperture upon removal of the dilator, thereby substantially preventing fluid flow through the central aperture.

9. An apparatus as recited in claim 1, the coring assembly further comprising a plug for closing the central aperture upon removal of the dilator, thereby substantially preventing fluid flow through the central aperture.

10. An apparatus as recited in claim 1, wherein the distal end of the dilator comprises a tapered conical profile configured to dilate the tissue upon advancement of the dilator within said tissue wall.

11. An apparatus as recited in claim 1, the central aperture of the cuff configured to allow advancement of an instrument through said tissue wall.

12. A system for delivering a ventricular assist device (VAD) through a tissue wall of the heart, comprising:
a dilator having a tapered distal end for piercing tissue in said tissue wall;
a cuff having a central aperture for receiving the cuff over the dilator; and
a coring handle releasably coupled proximal to the cuff to form a coring assembly;
wherein the coring assembly is configured to engage the dilator such that the dilator and coring assembly rotate as a single unit upon manual rotation of the dilator;
wherein in an assembled configuration, the coring assembly is configured to seat on the dilator at a location proximal to the distal end;
wherein the cuff and dilator in the assembled configuration are configured to be inserted into the tissue by introducing the distal end of the dilator into the tissue and advancing the distal end of the dilator to dilate the tissue until the cuff is seated within the tissue wall;
wherein the dilator is configured to be retracted from the coring assembly such that the cuff remains in the tissue wall to form a port into the heart via the central aperture of the cuff; and
wherein the coring handle is configured to be detached from the cuff upon removal of the dilator.

13. A system as recited in claim 12:
wherein the distal end of the dilator has one or more threads at said distal end; and
wherein the one or more threads are configured for engaging the tissue and advancing the dilator into the tissue upon rotation of the dilator.

14. A system as recited in claim 13:
wherein the cuff comprises one or more threads matching the one or more threads of the dilator; and
wherein the one of more cuff threads are configured to further advance the cuff into the tissue upon rotation of the dilator.

15. A system as recited in claim 14, wherein the coring handle comprises a keying slot configured to interface with a protrusion on the dilator for preventing radial and axial advancement of the cuff with respect to the dilator upon rotation and advancement of the dilator.

16. A system as recited in claim 15, wherein the keying slot of the coring handle and protrusion on the dilator are located such that the one or more threads of the dilator are aligned with the one or more threads of the cuff.

17. A system as recited in claim 15, said coring assembly further comprising a sewing ring for attaching the cuff to the tissue wall.

18. A system as recited in claim 12, wherein the dilator comprises a central through-hole for guiding the dilator over a guide-wire.

19. A system as recited in claim 12, the coring assembly further comprising a collapsible sleeve proximally coupled to the cuff for closing the central aperture upon removal of the dilator, thereby substantially preventing fluid flow through the central aperture.

20. A system as recited in claim 12, the coring assembly further comprising a plug for closing the central aperture upon removal of the dilator, thereby substantially preventing fluid flow through the central aperture.

21. A system as recited in claim 12, wherein the distal end of the dilator comprises a tapered conical profile configured to dilate the tissue upon advancement of the dilator within said tissue wall.

22. A system as recited in claim 12, the system further comprising a VAD:
wherein the central aperture of the cuff is configured to allow advancement of the VAD into the heart.

23. A system as recited in claim 22:
wherein the VAD is disposed on a distal end of a conduit;
wherein a plug is disposed on the conduit proximal to the VAD; and
wherein the plug is sized to form a seal to block flow of blood from the central aperture when the VAD is positioned within the heart.

* * * * *